United States Patent [19]
Visser

[11] Patent Number: 5,935,597
[45] Date of Patent: Aug. 10, 1999

[54] DRUG DELIVERY DEVICES AND METHODS FOR TREATMENT OF VIRAL AND MICROBIAL INFECTIONS AND WASTING SYNDROMES

[75] Inventor: Michelle Olga Patricia Giesteira Visser, Pretoria, South Africa

[73] Assignee: Cryopreservation Technologies CC, Riet fontein Pretoria, South Africa

[21] Appl. No.: 08/874,425

[22] Filed: Jun. 13, 1997

Related U.S. Application Data

[63] Continuation-in-part of application No. PCT/US96/19697, Dec. 13, 1996.

[30] Foreign Application Priority Data

Dec. 15, 1995 [ZA] South Africa ............... 95/10674
Jul. 5, 1996 [ZA] South Africa ............... 96/5755

[51] Int. Cl.⁶ ..................................... A61F 13/00
[52] U.S. Cl. .................. 424/449; 424/448; 424/422
[58] Field of Search ................... 424/448, 449, 424/422

[56] References Cited

U.S. PATENT DOCUMENTS

| | | | |
|---|---|---|---|
| 5,135,480 | 8/1992 | Bannon | 604/20 |
| 5,359,131 | 10/1994 | Cardin | 562/51 |
| 5,534,260 | 7/1996 | Petersen | 424/448 |

*Primary Examiner*—D. Gabrielle Brouillette
*Attorney, Agent, or Firm*—Ladas & Parry

[57] ABSTRACT

Novel drug delivery devices, methods and therapeutic compositions are described for treating viral and microbial infections and wasting syndromes in an animal, including a human patient. According to the invention, a polar compound such as dimethylformamide or dimethylsulfoxide is administered to a patient in need of treatment, preferably by a transdermal route. The invention further provides a vaccine prepared from antibodies harvested from the body of a patient treated by the method of the invention for a viral infection.

34 Claims, 4 Drawing Sheets

DRUG DELIVERY DEVICES AND METHODS FOR TREATMENT OF VIRAL AND MICROBIAL INFECTIONS AND WASTING SYNDROMES

1. CROSS-REFERENCE TO RELATED APPLICATIONS

This is a continuation-in-part of co-pending International Application No. PCT/US96/19697, filed Dec. 13, 1996, which is incorporated by reference herein in its entirety.

2. FIELD OF THE INVENTION

The present invention is directed to methods of treating an animal affected by a viral or microbial infection, particularly an infection with a retrovirus, such as HIV, or by a wasting syndrome, especially a wasting syndrome associated with HIV infection or malignancy, by administering a polar compound such as N,N'-dimethylformamide (DMF) or dimethylsulfoxide (DMSO). The invention also provides pharmaceutical preparations and drug delivery devices comprising a polar compound such as DMF or DMSO for treatment of an animal affected by a viral or other microbial infection or a wasting syndrome.

3. BACKGROUND OF THE INVENTION

3.1 THE HUMAN IMMUNODEFICIENCY VIRUS

Human immunodeficiency virus (HIV) induces a persistent and progressive infection leading, in the vast majority of cases, to the development of the acquired immunodeficiency syndrome (AIDS) (Barre-Sinoussi et al., 1983, Science 220: 868–870; Gallo et al., 1984, Science 224:500–503). There are at least two distinct types of HIV: HIV-1 (Barre-Sinoussi et al., 1983, Science 220:868–870; Gallo et al., 1984, Science 224:500–503) and HIV-2 (Clavel et al., 1986, Science 233:343–346; Guyader et al., 1987, Nature 326:662–669). In humans, HIV replication occurs prominently in $CD4^+$ T lymphocyte populations, and HIV infection leads to depletion of this cell type and eventually to immune incompetence, opportunistic infections, neurological dysfunctions, neoplastic growth, and ultimately death.

HIV is a member of the lentivirus family of retroviruses (Teich et al., 1984, RNA Tumor Viruses, Weiss et al., eds., CSH-press, pp. 949–956). Retroviruses are small enveloped viruses that contain a single-stranded RNA genome, and replicate via a DNA intermediate produced by a virally-encoded reverse transcriptase, an RNA-dependent DNA polymerase (Varmus, H., 1988, Science 240:1427–1439). Other retroviruses include, for example, oncogenic viruses such as human T-cell leukemia viruses (HTLV-1,-II,-III), and feline leukemia virus.

The HIV viral particle consists of a viral core, composed in part of capsid proteins designated p24 and p18, together with the viral RNA genome and those enzymes required for early replicative events. Myristylated gag protein forms an outer viral shell around the viral core, which is, in turn, surrounded by a lipid membrane envelope derived from the infected cell membrane. The HIV envelope surface glycoproteins are synthesized as a single 160 kilodalton precursor protein which is cleaved by a cellular protease during viral budding into two glycoproteins, gp41 and gp120. gp41 is a transmembrane glycoprotein and gp120 is an extracellular glycoprotein which remains non-covalently associated with gp41, possibly in a trimeric or multimeric form (Hammerskjold, M. and Rekosh, D., 1989, Biochem. Biophys. Acta 989:269–280).

HIV, like other enveloped viruses, introduces viral genetic material into the host cell through a viral-envelope mediated fusion of viral and target membranes. HIV is targeted to $CD4^+$ cells because a CD4 cell surface protein (CD4) acts as the cellular receptor for the HIV-1 virus (Dalgleish et al., 1984, Nature 312:763–767; Klatzmann et al., 1984, Nature 312:767–768; Maddon et al., 1986, Cell 47:333–348). Viral entry into cells is dependent upon gp120 binding the cellular CD4 receptor molecules (Pal et al., 1993, Virology 194:833–837; McDougal et al., 1986, Science 231:382–385; Maddon et al., 1986, Cell 47:333–348), explaining HIV's tropism for $CD4^+$ cells, while gp41 anchors the envelope glycoprotein complex in the viral membrane. The binding of gp120 to CD4 induces conformational changes in the viral glycoproteins, but this binding alone is insufficient to lead to infection (reviewed by Sattentau and Moore, 1993, Philos. Trans. R. Soc. London (Biol.) 342:59–66).

Studies of HIV-1 isolates have revealed a heterogeneity in their ability to infect different human cell types (reviewed by Miedema et al., 1994, Immunol. Rev. 140:35–72). The majority of extensively passaged laboratory strains of HIV-1 readily infect cultured T cell lines and primary T lymphocytes, but not primary monocytes or macrophages. These strains are termed T-tropic. T-tropic HIV-1 strains are more likely to be found in HIV-1 infected individuals during the late stages of AIDS (Weiss et al., 1996, Science 272:1885–1886). The majority of primary HIV-1 isolates (i.e., viruses not extensively passaged in culture) replicate efficiently in primary lymphocytes, monocytes and macrophages, but grow poorly in established T cell lines. These isolates have been termed M-tropic. The viral determinant of T- and M- tropism maps to alterations in the third variable region of gp1120 (the V3 loop)(Choe et al., 1996, Cell 85:1135–1148; Cheng-Mayer et al., 1991, J. Virol. 65:6931–6941; Hwang et al., 1991, Science 253:71–74; Kim et al., 1995, J. Virol., 69:1755–1761; and O'Brien et al., 1990, Nature 348:69–73). The characterization of HIV isolates with distinct tropisms taken together with the observation that binding to the CD4 cell surface protein alone is insufficient to lead to infection, suggest that cell-type specific cofactors might be required in addition to CD4 for HIV-1 entry into the host cell.

3.2 TREATMENT OF HIV INFECTION

HIV infection is pandemic and HIV-associated diseases represent a major world health problem. Although considerable effort is being put into the design of effective. Therapeutics, currently no curative anti-retroviral drugs against AIDS exist. In attempts to develop such drugs, several stages of the HIV life cycle have been considered as targets for therapeutic intervention (Mitsuya, H., et al., 1991, FASEB J. 5:2369–2381). Many viral targets for intervention with HIV life cycle have been suggested, as the prevailing view is that interference with a host cell protein would have deleterious side effects. For example, virally encoded reverse transcriptase has been one focus of drug development. A number of reverse-transcriptase-targeted drugs, including 2',3'-dideoxynucleoside analogs such as AZT, ddI, ddC, and d4T have been developed which have been shown to been active against HIV (Mitsuya, H., et al., 1991, Science 249:1533–1544).

The new treatment regimens for HIV-1 show that a combination of anti-HIV compounds, which target reverse transcriptase (RT), such as azidothymidine (AZT), lamivudine (3TC), dideoxyinosine (ddI), dideoxycytidine (ddC) used in combination with an HIV-1 protease inhibitor have a far greater effect (2 to 3 logs reduction) on viral load compared to AZT alone (about 1 log reduction). For example, impressive results have recently been obtained with a combination of AZT, ddI, 3TC and ritonavir (Perelson, A. S., et al., 1996, Science 15:1582–1586). However, it is likely that long-term use of combinations of these chemicals will lead to toxicity, especially to the bone marrow. Long-term cytotoxic therapy may also lead to suppression of $CD8^+$ T cells, which are essential to the control of HIV, via killer cell activity (Blazevic, V., et al., 1995, AIDS Res. Hum. Retroviruses 11:1335–1342) and by the release of suppressive factors, notably the chemokines Rantes, MIP-1$\alpha$ and MIP-1$\beta$ (Cocchi, F., et al., 1995, Science 270:1811–1815). Another major concern in long-term chemical anti-retroviral therapy is the development of HIV mutations with partial or complete resistance (Lange, J. M., 1995, AIDS Res. Hum. Retroviruses 10:S77–82). It is thought that such mutations may be an inevitable consequence of anti-viral therapy. The pattern of disappearance of wild-type virus and appearance of mutant virus due to treatment, combined with coincidental decline in $CD4^+$ T cell numbers strongly suggests that, at least with some compounds, the appearance of viral mutants is a major underlying factor in the failure of AIDS therapy.

Attempts are also being made to develop drugs which can inhibit viral entry into the cell, the earliest stage of HIV infection. Here, the focus has thus far been on CD4, the cell surface receptor for HIV. Recombinant soluble CD4, for example, has been shown to inhibit infection of $CD4^+$ T cells by some HIV-1 strains (Smith, D.H., et al., 1987, Science 238:1704–1707). Certain primary HIV-1 isolates, however, are relatively less sensitive to inhibition by recombinant CD4 (Daar, E., et al., 1990, Proc. Natl. Acad. Sci. USA 87:6574–6579). In addition, recombinant soluble CD4 clinical trials have produced inconclusive results (Schooley, R., et al., 1990, Ann. Int. Med. 112:247–253; Kahn, J. O., et al., 1990, Ann. Int. Med. 112:254–261; Yarchoan, R., et al., 1989, Proc. Vth Int. Conf. on AIDS, p. 564, MCP 137).

The late stages of HIV replication, which involve crucial virus-specific processing of certain viral encoded proteins, have also been suggested as possible anti-HIV drug targets. Late stage processing is dependent on the activity of a viral protease, and drugs are being developed which inhibit this protease (Erickson, J., 1990, Science 249:527–533).

Recently, chemokines produced by $CD8^+$ T cells have been implicated in suppression of HIV infection (Paul, W. E., 1994, Cell 82:177; Bolognesi, D. P., 1993, Semin. Immunol. 5:203). The chemokines RANTES, MIP-1$\alpha$ and MIP-1$\beta$, which are secreted by $CD8^+$ T cells, were shown to suppress HIV-1 p24 antigen production in cells infected with HIV-1 or HIV-2 isolates in vitro (Cocchi, F, et al., 1995, Science 270:1811–1815). Thus, these and other chemokines may prove useful in therapies for HIV infection. The clinical outcome, however, of all these and other candidate drugs is still in question.

Attention is also being given to the development of vaccines for the treatment of HIV infection. The HIV-1 envelope proteins (gp160, gp120, gp41) have been shown to be the major antigens for anti-HIV antibodies present in AIDS patients (Barin et al., 1985, Science 228:1094–1096). Thus far, therefore, these proteins seem to be the most promising candidates to act as antigens for anti-HIV vaccine development. Several groups have begun to use various portions of gp160, gp120, and/or gp41 as immunogenic targets for the host immune system. See for example, Ivanoff, L., et al., U.S. Pat. No. 5,141,867; Saith, G., et al., WO92/22,654; Shafferman, A., WO91/09,872; Formoso, C., et al., WO90/07,119. To this end, vaccines directed against HIV proteins are problematic in that the virus mutates rapidly rendering many of these vaccines ineffective. Clinical results concerning these candidate vaccines, however, still remain far in the future.

Thus, although a great deal of effort is being directed to the design and testing of anti-retroviral drugs, effective, non-toxic treatments are still needed.

3.3 WASTING SYDROMES

Wasting syndrome is a serious clinical problem characterized by a decrease in body mass of more than 10% from baseline body weight and a disproportionate loss of body mass with respect to body fat (Weinroth et al., 1995, Infectious Agents and Disease 4:76–94; Kotler and Grunfeld, 1995, AIDS Clin. Rev. 96:229–275). Thus, wasting is distinguished from starvation in which higher levels of body fat than body cell mass are depleted (Kotler et al., 1985, Am. J. Clin. Nutr. 42:1255–1265; Cahill, 1970, N. Engl. J. Med. 282:668–675). Wasting is associated with a variety of conditions, including HIV infection, other infectious diseases, sepsis, cancer, chronic cardiovascular disease and diarrhea (Kotler et al., 1989, Am. J. Clin. Nutr. 50:444–447; Heymsfield et al., 1982, Am. J. Clin. Nutr. 36:680–690). Importantly, wasting is a significant factor in the mortality of patients suffering from infections or cancer. In fact, body cell mass depletion has a linear relationship to time of survival in AIDS patients (Kotler et al., 1989, Am. J. Clin. Nutr. 50:444–447).

The cause of wasting syndrome in AIDS and other conditions is unclear and is most likely multifactorial. Metabolic abnormalities, irregular levels of hormones and cytokines, and malabsorption have all been implicated in wasting syndrome. Not all AIDS patients suffer from wasting, suggesting that the cause of the wasting is not HIV itself. Most cases of HIV associated wasting syndrome are apparently caused by complications of AIDS, such as secondary infections and gastrointestinal disease (Kotler and Grunfeld, 1995, AIDS Clin. Rev. 96:229–275).

Current and potential therapies for wasting syndromes include nutritional support, appetite enhancers such as dronabinol and megestrol acetate, anabolic therapies, such as growth hormone, and cytokine inhibitors. However, mixed results have been obtained with nutritional support and appetite enhancers in that patients tended to gain only fat and not overall body mass. Administration of growth hormone, and cytokine inhibitors are still being tested and may pose a risk of side effects (Kotler and Grunfeld, 1995, AIDS Clin. Rev. 96:229–275; Weinroth et al., 1995, Infectious Agents and Disease 4:76–94).

Thus, treatment of wasting is critical to the survival and well-being of patients suffering from serious diseases such as cancer and AIDS; thus, there is a need for safe and effective therapies for wasting syndrome associated with cancer, AIDS and other infectious diseases.

3.4 PROPERTIES OF DIMETHYLFORMAMIDE AND OTHER POLAR COMPOUNDS

N,N'-dimethylformamide (DMF) (molecular formula: $C_3H_7ON$) is a colorless, polar, hygroscopic liquid with low volatility and a boiling point of 152.5–153.5° C. It is freely miscible with water, alcohols and some hydrocarbons. DMF is generally used as a polar solvent and is readily absorbed through the skin, by inhalation, and upon oral ingestion. DMF is rapidly metabolized, mainly in the liver, and excretion occurs principally in the urine. In rat, mouse, hamster and man the main metabolites of DMF are N-hydroxymethyl-N-methylformamide (HMMF), N-methylformamide (NMF), and N-acetyl-S-(N-methylcarbamoyl)cysteine (AMCC), as well as dihydroxymethylformamide (DHMF) and N-hydroxymethylformamide (HMF). Unchanged DMF is excreted in the urine as a small fraction of an administered dose of DMF.

DMF has low acute dermal, oral and inhalation toxicity. It is considered to be a mild to moderate skin and eye irritant and readily permeates the skin. There is no indication of skin sensitizing properties. The principal toxic effect of DMF and its metabolites is on the liver; DMF is well known to cause reversible hepatic damage associated with typical clinical complaints, classical biochemical changes in the blood, and the appearance of hepatocyte necrosis in liver biopsies. DMF is teratogenic, but is not thought to be a mutagen or a carcinogen.

Viza et al. have reported that DMF and DMSO inhibit in vitro replication of HIV and Human Herpes Virus 6 (HHV-6) in certain cultured cell lines. (See Viza et al., 1990, AIDS Res. Hum. Retroviruses 6:131–132; Viza et al., 1989, AIDS-FORSCHUNG 4:349–352; Viza et al., 1992, Antiviral Res. 18:27–38 and erratum at 19:179).

DMF has been described as an in vitro differentiating agent for certain transformed cells in culture (See Koeffler, 1983, Blood 62:709–721; Calabresi et al., 1979, Biochem. Pharmacol. 28:1933–1941). When added to certain malignant cells in vitro, DMF has been reported to reduce their tumorigenicity upon subsequent inoculation into nude mice (See Dexter, 1977, Cancer Res. 37:3136–3140; Dexter et al., 1979, Cancer Res. 39:1020–1025). Upon intraperitoneal injection into nude mice, DMF and NMF have been reported to slow the growth of certain human cancer xenografts (See Van Dongen et al., 1989, Int. J. Cancer 43:285–292; Braakhuis et al., 1989, Head & Neck 11:511–515; Van Dongen et al., 1988, Acta Otolaryngol. 105:488–493; Dexter et al., 1982, Cancer Res. 42:5018–5022). However, the toxic side-effects of formamide and its N-methyl derivatives in a mouse sarcoma allograft model led investigators to conclude that these agents were unlikely to prove therapeutically useful (See Clarke et al., 1953, Proc. Sec. Exp. Biol. Med. 84:203–207).

Attempts at treating human cancer patients with DMSO led to the conclusion that no objective response had been shown (See Spremulli & Dexter, 1984, J. Clin. Oncol. 2:227–241). Oral administration of NMF to human patients with cancer of the head and neck was reported as resulting in hepatotoxicity with no beneficial response (see Vogel et al., 1987, Invest. New Drugs 5:203–206), or with only minimal activity (See Planting et al., 1987, Cancer Treat Rep. 71:1293–1294).

U.S. Pat. No. 3,551,154 discloses the use of DMF as a penetration enhancer to promote transdermal absorption of topically applied medications. U.S. Pat. No. 4,855,294 discloses the use of glycerin to mitigate the skin irritation arising from the use of DMSO and DMF as penetration enhancers to promote transdermal absorption of topically applied medications. The use of DMSO as a penetration enhancer to promote transdermal absorption of antiviral agents is discussed in Woodford & Barry, 1986, J. Toxicol. Cut. & Ocular Toxicol. 5:167–177.

Citation or identification of any reference in Section 3 (or any other section) of this application shall not be construed as an admission that such reference is available as prior art to the present invention.

4. SUMMARY OF THE INVENTION

The present invention is directed to methods, compositions and drug delivery devices for treating an animal affected by a viral or other microbial infection, especially an infection with a retrovirus such as HIV. The invention also provides methods, compositions and drug delivery devices for treating an animal affected by a wasting syndrome, such as wasting associated with HIV infection or malignancy.

According to the present invention, there is administered to an animal in need of treatment a composition comprising N,N'-dimethylformamide (dimethylformamide, DMF); N-hydroxymethyl N-methylformamide (HMMF); N-hydroxymethylformamide (HMF); dihydroxymethylformamide (DHMF); N-acetyl, S-(N-methylcarbamoyl) cysteine (AMCC); N-methylformamide (NMF); dimethylsulfoxide (DMSO); formamide; acetamide; methylacetamide; dimethylacetamide; diethylacetamide; isopropylacetamide; diisopropylacetamide; N-acetylpiperidine; N-(β-hydroxyethyl)acetamide; N,N'-di(β-hydroxyethyl)acetamide; N-acetylmorpholine; acrylamide; propionamide; N-fluoromethyl-N-methyl-formamide; pyridine-N-oxide; or any agent selected from the group consisting of amides of the general formula $R_3$—CO—$NR_1R_2$, in which $R_1$ and $R_2$ are independently selected from the group consisting of H, methyl, halomethyl, saturated and unsaturated $C_2$–$C_3$ alkyl groups, and hydroxylated alkyl groups; or $R_1$ and $R_2$ are together selected from the group consisting of $(CH_2)_4$, $(CH_2)_5$, and $(CH_2)_2O(CH_2)_2$; and $R_3$ is selected from the group consisting of H, methyl, and saturated and unsaturated $C_2$–$C_3$ alkyl groups. The therapeutic composition may comprise a mixture of any two or more of the aforementioned compounds.

In a patient infected with HIV, the therapeutic regimen may optionally combine a composition of the present invention with one or more additional agents effective for treating HIV infection, including but not limited to agents selected from the group consisting of nucleoside analog reverse transcriptase inhibitors, non-nucleoside reverse transcriptase inhibitors, and protease inhibitors, in any desired combination.

The invention also extends to a vaccine prepared from antibodies that are obtained from the body of an animal after treatment with a composition of the invention for a viral infection.

5. BRIEF DESCRIPTION OF THE FIGURES

The present invention may be more fully understood by reference to the following detailed description of the invention, examples of specific embodiments of the invention and the appended figures in which.

6. DETAILED DESCRIPTION OF THE INVENTION

The present invention provides methods, compositions and drug delivery devices for treating viral and microbial infections. In one embodiment, the infection to be treated is an infection with a retrovirus such as HIV, including an asymptomatic infection, a latent infection, an infection accompanied by one or more symptoms of the AIDS-related complex, and an infection accompanied by clinical AIDS. Alternatively, the infection to be treated is any other viral or microbial infection, including infection with rubella, a herpesvirus such as Human Herpes Virus 6, the Epstein-Barr virus or cytomegalovirus, infection with any virus having a capsid protective coating, and any opportunistic infection associated with disease of the immune system, such as an opportunistic infection in a patient infected with HIV.

The present invention also provides methods, compositions and drug delivery devices for treatment or prevention of any disease or disorder characterized by a loss of body mass. Particular conditions that can be treated by the methods and compositions of the invention include, but are not limited to, wasting associated with viral (e.g. HIV), bacterial, or any other types of infection or sepsis, cachexia associated with malignancy, chemotherapy or radiation therapy, wasting associated with chronic cardiovascular disease, wasting caused by exposure to toxic or radioactive substances, and wasting associated with diarrhea and other gastrointestinal disorders.

The subject to be treated may be any animal, including but not limited to a monkey, cow, sheep, ox, pig, horse, cat, dog, chicken and the like, and is preferably a mammal, more preferably a primate, and most preferably a human adult or child, for instance a human child weighing at least 3 kg. As used herein, the term "patient" refers to any animal in need of treatment according to the methods or compositions of the present invention.

According to the present invention, there is administered a therapeutic composition comprising DMF; HMMF; HMF; DHMF; AMCC; NMF; DMSO; formamide; acetamide; methylacetamide; dimethylacetamide; diethylacetamide; isopropylacetamide; diisopropylacetamide; N-acetylpiperidine, N-($\beta$-hydroxyethyl)acetamide; N,N'-di ($\beta$-hydroxyethyl)acetamide; N-acetylmorpholine; acrylamide; propionamide; N-fluoromethyl-N-methyl-formamide; pyridine-N-oxide; any agent selected from the group consisting of amides of the general formula $R_3$—CO—$NR_1R_2$, in which $R_1$ and $R_2$ are independently selected from the group consisting of H, methyl, halomethyl, saturated and unsaturated $C_2$–$C_3$ alkyl groups, and hydroxylated alkyl groups; and $R_3$ is selected from the group consisting of H, methyl, and saturated and unsaturated $C_2$–$C_3$ alkyl groups; or any agent selected from the group consisting of amides of the general formula $R_3$—CO—$NR_1R_2$, in which $R_1$ and $R_2$ are independently selected from the group consisting of H, methyl, halomethyl, saturated and unsaturated $C_2$–$C_3$ alkyl groups, and hydroxylated alkyl groups; or $R_1$ and $R_2$ are together selected from the group consisting of $(CH_2)_4$, $(CH_2)_5$, and $(CH_2)_2O(CH_2)_2$; and $R_3$ is selected from the group consisting of H, methyl, and saturated and unsaturated $C_2$–$C_3$ alkyl groups.

In one specific embodiment, at least one of $R_1$ and $R_2$ is a methyl group. In another specific embodiment, at least one of $R_1$ and $R_2$ is a a fluorinated $C_1$–$C_3$ alkyl group. The therapeutic composition may comprise a mixture of any two or more of the aforementioned compounds. Especially preferred is a composition comprising DMF.

For treatment of an animal infected with HIV, the therapeutic regimen may optionally include, in addition to a composition of the present invention, one or more other agents effective for treating HIV infection, for instance one or more nucleoside analog reverse transcriptase inhibitors such as zidovudine (AZT, ZDV), zalcitabine (ddC), didanosine (ddI), lamivudine (3TC), stavudine (d4T); one or more non-nucleoside reverse transcriptase inhibitors such as nevirapine, delavirdine, loviride, atevirdine, pyridinone; one or more protease inhibitors such as saquinavir, indinavir, ritonavir, nelfinavir; or any combination of the aforesaid or other anti-HIV therapeutic agents. The composition of the present invention and the additional anti-HIV therapeutic agent or agents may be administered simultaneously, sequentially, or in cycles of treatment according to any desired therapeutic protocol, and may be given by the same route of administration or by any desired combination of routes.

The compositions of the present invention may be administered by any desired enteral or parenteral route, including but not limited to transdermal, intradermal, subcutaneous, intramuscular, intraperitoneal, intravenous, intranasal, epidural, intralymphatic and oral routes. The compounds may be administered by any convenient method, for example by infusion or bolus injection, by absorption through epithelial or mucocutaneous linings (e.g., oral, gastric, intestinal or rectal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and the formulation may include an aerosolizing agent. If desired, any two or more routes of administration may be employed simultaneously, sequentially, or in cycles of treatment according to any therapeutic protocol.

In a specific embodiment, it may be desirable to administer a composition of the invention locally to the area in need of treatment; this may be achieved, for example and not by way of limitation, by topical application, by injection, by means of a catheter, by means of a suppository, or by means of an implant, said implant being of a porous, non-porous, or gelatinous material, including membranes, such as sialastic membranes, or fibers.

In another embodiment, a composition of the invention can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, a composition of the invention can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

The present invention also provides pharmaceutical preparations. Such preparations comprise a therapeutically effective amount of a composition of the invention and a pharmaceutically acceptable carrier. In a specific embodiment, the term "pharmaceutically acceptable" means approved by a regulatory agency of the Federal or a state or other government or listed in the U.S. Pharmacopeia or other generally recognized pharmacopeia for use in animals, and more particularly in humans. The term "carrier" refers to a diluent, adjuvant, excipient, or vehicle with which the composition of the present invention is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical preparation is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The pharmaceutical preparation, if desired, can also contain minor amounts of wetting or emulsifying agents, or pH buffering agents. These preparations can take the form of solutions, suspensions, emulsion, tablets, pills, capsules, powders, sustained-release formulations and the like. The preparation can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such preparations will contain a therapeutically effective amount of the Therapeutic, preferably in purified form, together with a suitable amount of carrier so as to provide the form for proper administration to the patient. The formulation should suit the mode of administration.

The compositions of the present invention may be administered transdermally. In one embodiment, a composition of the invention is directly applied to the skin. In another embodiment, a composition of the invention is applied to a reservoir (e.g. a cotton wool pad, a synthetic polymer such as Teflon™, or any suitable adsorbant) that is applied to the skin, preferably under an occlusive dressing. In a specific embodiment, a composition of the present invention is applied o the skin by means of a dermal patch. The concentration of he active therapeutic agent in the composition that is applied to the skin, contained in or adsorbed onto the reservoir, or contained in the dermal patch may be about 10–100%, preferably at least 50%, more preferably at least 90%.

In a preferred embodiment, a polar compound such as DMF is administered transdermally using any suitable drug delivery device, for example by applying one or more dermal patches. The dermal patch may optionally comprise a backing, a reservoir such as an adsorbant impregnated with a polar compound of the invention, and a permeable membrane that is placed in contact with the skin. The backing may be of any material, such as a natural or synthetic polymer, that resists chemical attack by the polar compound. Especially preferred is a backing of high density polyethylene. The adsorbant may be a colloidal substance, for instance diatomaceous earth or colloidal silicon dioxide. The permeable membrane may be of any material that chemically resists the polar compound and may optionally be provided with pores. In a preferred embodiment, the permeable membrane is a TEFLON™ (polytetrafluoroethylene) membrane having pores with a diameter of about 0.1 µm, a diameter of about 0.5 µm, or a diameter within the range of from about 0.1 µm to about 0.5 µm. The patch may be self-adhesive or may be held in contact with the skin by an applicator, such as a wrapping or bandage, including without limitation an elastic bandage or an adhesive bandage; an Elastoplast™ bandage is suitable for this purpose. Preferably, the patch contains a greater quantity of polar compound than is intended to be delivered through the skin of the patient to be treated; for instance, the patch may contain about 50% more of the polar compound than is intended to be delivered. The patch may be of any desired size and shape, and may for instance take the form of a disk approximately 9 cm in diameter.

In one embodiment, the patch comprises a polar compound, such as DMF, and at least one other pharmacologically active agent, for instance an local anti-irritant such as glycerine. In another embodiment, the patch comprises a polar compound, such as DMF, and has no other pharmacologically active agent present. In a further embodiment, the patch comprises a polar compound, such as DMF, and has present no other pharmacologically active agent that is capable of being systemically absorbed through the skin, or has present no other pharmacologically active agent in an amount that is systemically effective after transdermal absorption. In yet another embodiment, the patch comprises a polar compound, such as DMF, and has present no other systemically active pharmacological agent. In yet a further embodiment, the patch comprises a polar compound, such as DMF, and has present no other antiviral agent, for instance acyclovir or arildone.

The present invention thus provides a dermal patch comprising a polar compound, such as DMF, in an amount that is effective for treating a viral or microbial infection (for example an infection with HIV) in a human adult or a human child. The present invention further provides a dermal patch comprising a polar compound, such as DMF, in an amount that is effective for treating a wasting syndrome in a human adult or a human child. In one embodiment, the patch contains at least 0.25 g of a polar compound such as DMF, preferably at least 0.5 g, more preferably at least 1 g, and still more preferably at least 5 g, for instance 5–15 g of a polar compound such as DMF.

To minimize evaporative loss of the polar compound, the patch may optionally be stored in a sealed container, such as a sealed polymer bag. If desired, each patch may be individually sealed for convenience of use. Optionally, the patches may be refrigerated prior to use, for instance at about 4° C., so as to reduce evaporative loss of the polar compound. Preferably, the patches are prepared within 24 hours of use and are stored in a sealed container at 4° C.; however, patches are stable for one or more weeks when stored in a sealed container at 4° C. Prior to applying a patch, an area of skin is preferably washed with a mild soap and water, rinsed to remove soap residue, thoroughly dried, and then hydrated with a suitable skin lubricant and moistening agent, such as KY™ jelly. The patch is then removed from the packing material and applied so that the permeable membrane contacts the prepared skin surface. The patch may be held in place with an applicator. After a desired dosage period, the patch is removed. After removal of the patch, the treated area may be thoroughly washed with a mild soap and water to remove any residue of the polar compound.

The compositions of the present invention may be administered at any desired interval, for instance once every two or three weeks; once, twice or three times per week; every second day; or daily. Preferably, a composition of the invention is administered in a dose that results in a peak plasma level of about 2–200 mg/l, more preferably about 100–200 mg/l, still more preferably about 150 mg/l of the active ingredient of the composition, such as DMF. Especially preferred is a peak plasma level of 100–150 mg/l or 150–200 mg/l of DMF. As used herein, the term "ppm" refers to parts per million by weight, and is in practice equivalent to mg/l.

For transdermal administration of a polar compound, the rate of absorption is determined by the skin of the subject. Upon exposure to the human skin, liquid DMF is absorbed at a steady-state rate of approximately 9.4 mg/cm$^2$/hour (see Mraz and Nohova, 1992, Occup. Env. Health 64:85–92). Accordingly, the desired rate of absorption may be achieved by controlling the surface area of the skin exposed to the drug, as by determining the area of each patch and the number of patches applied to the skin. For example, two patches of diameter 9 cm will expose a total skin surface area of 127 cm$^2$ to the polar compound; for DMF, this will result in an absorption rate of about 1.2 g of DMF per hour. An initial dose of about 15 mg/kg of DMF is especially preferred.

In one embodiment, a patient weighing about 72 kg is initially treated with DMF by administering two 9 cm diameter dermal patches for one hour, resulting in an initial adsorbed dose of about 1.2 g of DMF, equivalent to about 16.7 mg/kg. The number of patches may be scaled up or down, and a longer or shorter initial period of exposure used, according to the body weight of the patient being treated. This starting dose may be repeated at any desired interval, as described above, and preferably is given at weekly intervals. Preferably, the patient is monitored for at least 72 hours after administration of DMF for signs of toxicity, such as liver toxicity, for example by monitoring the serum or plasma levels of enzymes such as aspartate aminotransferase (AST), alanine aminotransferase (ALT), γ-glutamyl transferase (γAGT) and alkaline phosphatase, proteins such as albumin, or substances such as conjugated or unconjugated bilirubin. Preferably, serum or plasma levels of AST and ALT do not exceed five times the upper limit of normal as determined by the reference range of the laboratory and population in question; more preferably serum or plasma levels of AST and ALT do not exceed three times the upper limit of normal, most preferably AST and ALT are not elevated above normal levels or above pre-treatment levels. The dose of DMF may be escalated by applying the patches for successively longer periods; in one embodiment the patches are applied for two hours, then four hours, then six hours, and so on; in another embodiment, the period of exposure is successively doubled. Preferably, the patient is monitored prior to any dose escalation, in order to detect any signs of toxicity. If desired, the dose may be escalated at weekly intervals. The dose may be escalated in this manner until the dose is calculated to be about 150 mg/kg/dose; or until a desired peak plasma level, for instance 100–150 or 150–200 mg/l is achieved; or until the period of exposure is about 6 hours or about 8 hours. One should be cautious before increasing the dose above 240 mg/kg/dose.

7. EXAMPLE
TREATMENT OF HIV INFECTION BY TRANSDERMAL ADMINISTRATION OF N,N'-DIMETHYLFORMAMIDE (DMF)

Patients infected with HIV-1 were treated with dimethylformamide (DMF) by the application of skin patches impregnated with a dimethylformamide gel to the patient's body. N-acetyl-cysteine-glutathione and/or essential phospholipids were administered (orally or intravenously) to the patients at a dosage of 250 mg to 300 mg daily as a liver booster. Instead or in addition, glutamine may also be administered to the patient as a liver booster.

Figure 1:
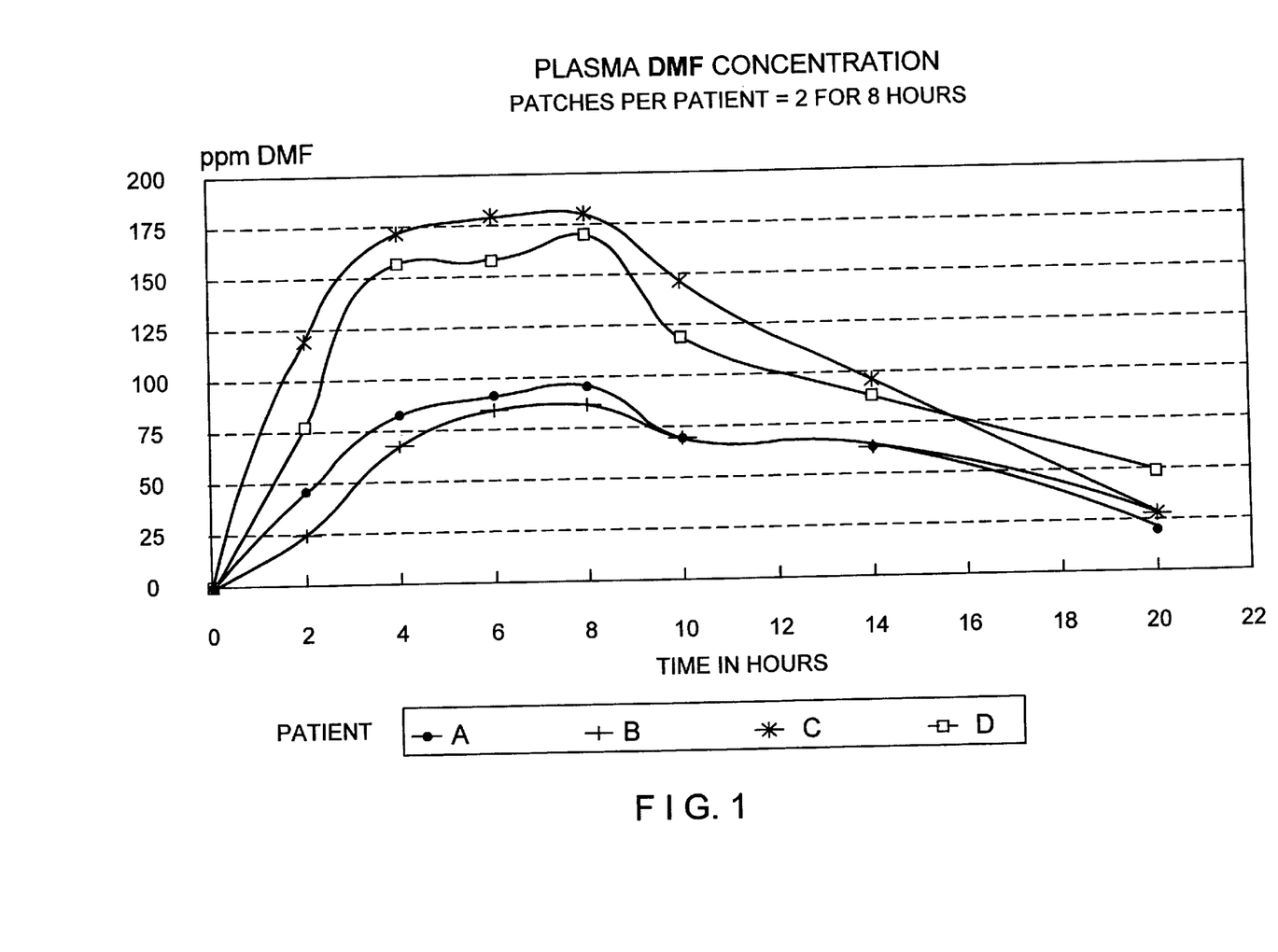
FIG. 1 illustrates plasma concentrations of DMF as a function of time in 4 patients treated with 2 DMF dermal patches for 8 hours.
Figure 2:
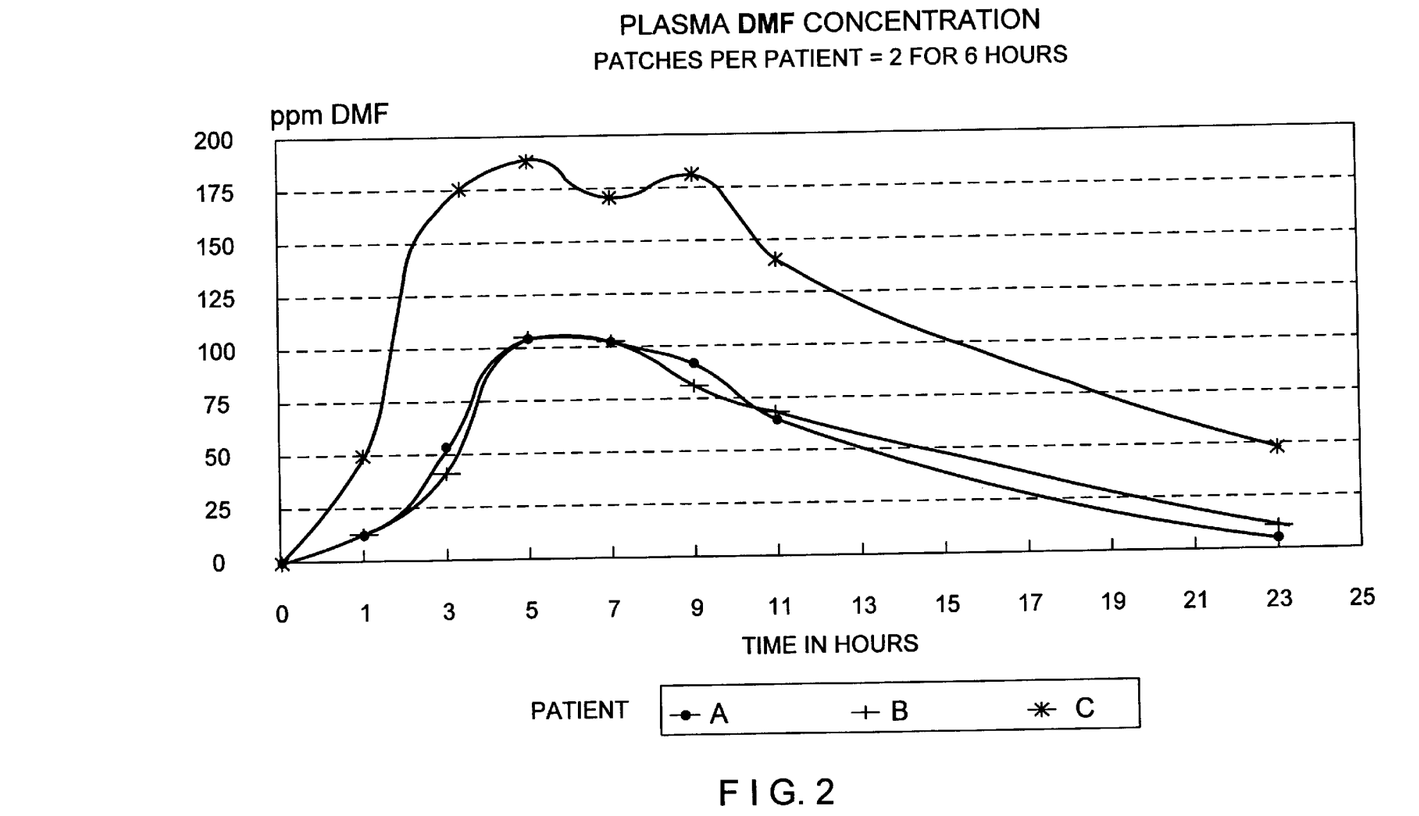
FIG. 2 illustrates plasma concentrations of DMF as a function of time in 3 patients treated with 2 DMF dermal patches for 6 hours.

Two skin patches were applied to different parts of the patient's body, for example to the forearm. Each skin patch contained about 7,06 g of gel comprising DMF (92,5% m/m) and colloidal silicon dioxide (7,5% m/m). The gel served to prevent leakage of liquid DMF from the patches. The patches were manufactured at most 12 hours prior to use as DMF evaporates rapidly. The intended level of DMF in the patient's blood was 100 ppm. For a patient weighing about 60 kg, an amount of about 14 g over a period of 12 hours is required to produce a level of 100 ppm. Based on studies by Marz and Nohova the surface area required to absorb this amount in about 127,2 cm$^2$. To obtain a blood level of 100 ppm about 1,272 g of DMF must be absorbed per hour, thus each sticker requires about 7,064 g DMF to deliver the required amount, having a surface area of 6,36 cm$^2$ (each sticker). DMF absorption rate is 9.4 mg/cm$^2$/hour. In theory this treatment will deliver 125–135 ppm, but due to evaporation of the DMF, 100 ppm was obtained. Absorption capability varies from patient to patient depending on factors such as skin-type and skin thickness. To obtain the desired levels of DMF in the patients, plasma DMF concentrations were monitored for each patient and treatment adjusted accordingly depending on the DMF level of each patient. FIG. 1 shows the plasma DMF levels of 4 patients treated with 2 dermal DMF patches for 8 hours. FIG. 2 shows the plasma DMF levels of 3 patients treated with 2 dermal DMF patches for 6 hours.

The stickers were thus each loaded with about 7,064 g of the gel of DMF and silicon dioxide. Each patch was applied for a period of 12 hours, either once per week over a period of 12 weeks, or twice per week over a period of 6 weeks.

Figure 3:
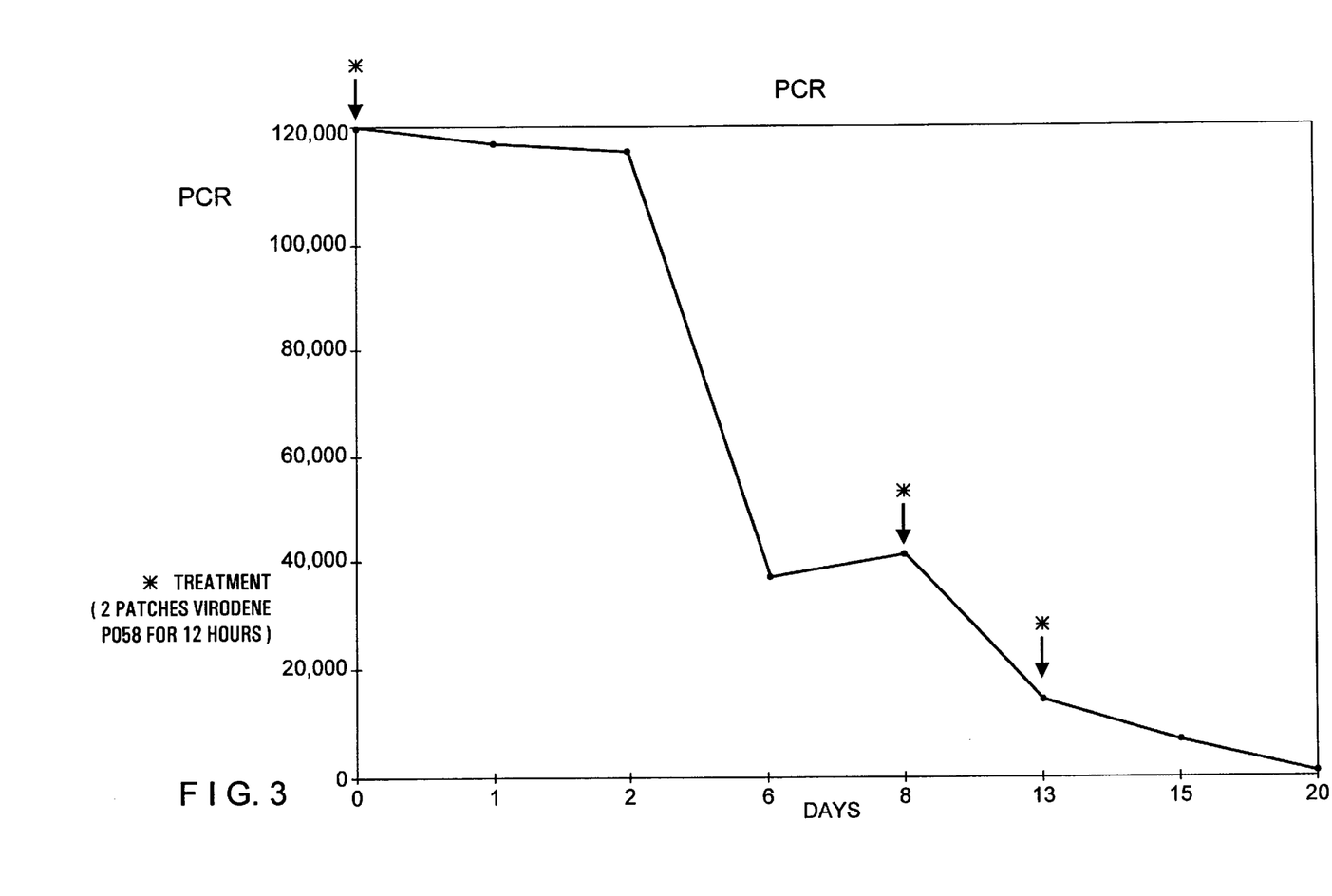
FIG. 3 illustrates HIV-1 viral load as measured by quantitative PCR in a patient treated with transdermal DMF. Two DMF patches were placed against the skin of the forearm for 12 hours on days 0, 8, and 13 (indicated by arrows).

Blood tests in certain patients indicated an increase in CD4 T-cell counts from 350 to 1000, and a rapid reduction of PCR (Polymerase chain reaction) (viral load) of 120,000 to 500/ml within three weeks with as little as three treatments. FIG. 3 shows serial quantitative PCR measurements of HIV-1 viral load in a patient prior to treatment and following three treatments with 2 dermal DMF patches for 12 hours. The PCR test conducted was the Roche amplicor HIV monitor. A viral load of <500/ml plasma is considered to be undetectable.

Some patients undergoing treatment had severe acne or displayed German measles symptoms before treatment. When treated with DMF so that the DMF level in the patient's blood was 50–100 ppm, the German measles symptoms and the severe acne cleared up or disappeared within 7 days.

Prior to the treatment with dimethylformamide, a comprehensive base-line clinical and psychological evaluation of the patient was conducted. The evaluation provided base-line biochemical and hematological data on the patient. Detailed virological serology (HIV-1) tests were also conducted to determine the patient's total body virus count, and these tests were conducted on a weekly basis, or as per treatment.

The concentration of DMF in the patient's blood was determined hourly during the period of treatment. An intravenous line was introduced each morning to take blood samples and was kept open with an infusion of Normal Saline at a rate of 20 ml/hour and daily monitoring of the active metabolite AMCC (eg by 4-hourly urine sampling) derived from the DMF was also conducted. Subsequent applications of DMF were adjusted in accordance with measured changes in blood level DMF concentration resulting from changes in absorption variables and daily full hematological and biochemical profiles were conducted to detect any changes in liver function. Daily full clinical and psychological evaluations were also conducted.

A daily virological serology workout to establish total body virus count and to monitor improvements in the immune status of the patient (CD4+ T-helper cells) and prognostic factors were also conducted. The serology workout was based on p24 antigen and quantitative PCR or, optionally, by other methods. A weekly determination of CD4 counts and Beta-2-macroglobulin was also conducted specifically to monitor improvements in the patient's immune status and prognosis. All clinical and laboratory data were fed into a centralized data system to facilitate rapid response to any detrimental change so as to curtail treatment to maximize clinical effect and minimize potential side effects.

The tests included
a) Serum: Na, K, Cl, $CO_2$, Urea, Urate, Creatinine, Ca, Mg, Phosphate, Total and Conjugated Bilirubin;
b) Hematology: Hemoglobin, Red cell count, Hematocrit, MCV, MCH, MCHC, RDW;
c) Serum Protein Electrophoresis: Total Proteins, Albumin, Total Globulin, Alpha1 Globulin, Alpha2 Globulin, Beta Globulin, Gamma Globulin;
d) White cell analysis: Differential white cell count, Absolute Neutrophil, Lymphocyte, Monocyte, Eosinophil and Basophil counts;
e) Liver Enzymes: Alk. Phos, Gamma GT, ALT (SGPT), AST (SGOT), LDH;
f) Other: Cell markers, PCR, Beta2-Microglobulin, p24 Antigen, C-Reactive protein, CK-MB concentration;
g) Blood analysis for DMF levels;
h) Urine analysis for AMCC levels It appears as if DMF acts as at least one of a reverse transcriptase inhibitor and a protease inhibitor. In vitro tests were conducted and it appears that the solvent properties of DMF dissolve the virus particles, e.g. the capsid.

8. EXAMPLE
TREATMENT OF HIV INFECTION BY TRANSDERMAL ADMINISTRATION OF N,N'-DIMETHYLFORMAMIDE (DMF)

A pilot study was conducted to evaluate the efficacy of transdermal DMF in the treatment of patients infected with HIV. Informed consent was obtained from each patient. Seropositive status was verified by Western blot using a commercial kit for detecting antibodies to p24 (Abbott Diagnostics) and the presence of HIV-1 was documented by quantitative PCR using a commercial kit (Roche Amplicor).

DMF as obtained commercially (Sigma-Aldrich) and in plasma samples was analyzed by mass spectroscopy/gas chromatography (GC/MS), using a Varian 9600 gas chromatograph, OV 351 column, Carbowax-PEG capillary column, and Finnegan Mat ITS40 ion trap detector. Operational parameters were as follows: GC temperature program: 60° C. for 1 min. followed by a temperature gradient of 9.4° C./min. for 20 min. MS ionization method: electron impact; mass range: 40–80 mass units; 1 scan/sec; peak threshold: 3 counts/sec; background mass: 69 mass units. A stock solution of dimethylacetamide was used as an internal standard. All samples were extracted with an organic solvent containing the internal standard, allowed to precipitate for 30 min. in a refrigerator, and centrifuged at 3000×g for 5 min. before transfer to GC vials for injection. Retention time of the DMF peak relative to the internal standard was 3.26 minutes; the calibration curve showed a correlation of 0.98. Quantitation of DMF appeared linear up to 100 mg/l and the lower limit of detection was estimated at 0.5 mg/l based on a signal-to-background ratio of 3:1.

Dermal patches 9 cm in diameter were used within 12 hours of manufacture. Each patch had a backing of high density polyethylene (0.245 g), a permeable membrane of TEFLON™ (Polytetrafluoethylene) (pore size 0.2 $\mu$m; 0.268 g) for placement against the skin, and contained 0.573 g of colloidal silicon dioxide impregnated with 7.067 g DMF between the backing and the permeable membrane. The patches were visually inspected to verify the absence of leakage and were weighed on an analytical balance to verify less than 10% deviation from a total mass of 8.153 g. The patches were applied to the skin of the forearm and secured with Elastoplast™ bandages. Either one or two patches were used for the initial dose, as determined from the predicted skin transfer rate of 9.4 mg/cm$^2$/hr and the patient's body weight.

A staged dose of DMF was used, with two-hourly blood and urine sampling to determine peak plasma DMF levels. Patients were clinically monitored for any toxic side-effects and were kept under comprehensive biochemical surveillance while the dosage was increased as necessary to achieve a peak plasma DMF level of 100–120 ppm. Once the correct dosage was established, transdermal DMF was given once a week. Initial evaluation included daily determination of:
a) vital signs and body weight;
b) clinical checklist and Karnofsky score;
a) full blood count and erythrocyte sedimentation rate;
b) serum urea, creatinine, glucose, sodium, potassium, ALT, AST, alkaline phosphatase and total bilirubin;
c) Coulter analysis of CD4+ and CD8+ counts and CD4/CD8 ratio;
d) Quantitative estimates of HIV-1 load by PCR (Roche Amplicor) and analysis of antibody to p24 (Abbott);
e) Urinalysis (Dipstix).

At each weekly visit, the patients were evaluated for adverse effects, virtually all these tests were repeated, and blood and urine were collected for measurement of DMF and its metabolites.

Patient 1 began the protocol with a clinical diagnosis of AIDS, and complained of respiratory difficulty. Two DMF patches were administered once a week, for an average exposure period of 8 hours. The average weekly dose of DMF was 8.97 g and the resulting peak plasma DMF level averaged 121 mg/l. After 7 weeks, the patient's CD4+ T cell count had increased from 39 to 138 cells/$\mu$l, the PCR-measured viral load had decreased from 222,000 to 160,000 copies/ml, and the patient's weight had increased from 74.2 to 100 kg. The patient's appetite had improved, the respiratory difficulties had resolved, the patient appeared clinically well and started exercising again.

Patient 2 began the protocol complaining of loss of strength, inability to sleep, pains in the arms and legs, and had herpes sores in the mouth. One DMF patch was administered per week, for an average exposure period of 8 hours. The average weekly dose of DMF was 7.12 g and the resulting peak plasma DMF level averaged 125 mg/l. After 9 weeks, the patient's CD4+ T cell count has increased from 460 to 720 cells/μl, the PCR-measured viral load had decreased from 29,000 to 13,000 copies/ml, and the patient's weight had increased from 58.4 to 63.0 kg. The patient's herpetic sores had resolved, the limb pains had disappeared and the patient appeared clinically well.

Patient 3 began the protocol in relatively good health, complaining principally of pains in the arms and legs and inability to sleep. Two DMF patches were administered once a week, for an average exposure period of 8 hours. The average weekly dose of DMF was 6.11 g and the resulting peak plasma DMF level averaged 75 mg/l. After 9 weeks, the patient's CD4+ T cell count had increased from 140 to 640 cells/μl and the PCR-measured viral load had decreased from 250,000 to 50,000 copies/ml. After 10 weeks the patient's weight had increased from 81.9 to 96.0 kg, the patient was clinically well and no longer complained of pain in the limbs.

Patient 4 began the protocol with secondary infections (including herpes), anemia, diarrhea and acne. Two DMF patches were administered once weekly, for an average exposure period of 8 hours. The average weekly dose of DMF was 7.33 g and the resulting peak plasma DMF level averaged 90 mg/l. After 18 weeks, the patient's CD4+ T cell count had increased from 249 to 450 cells/μl, the PCR-measured viral load had decreased from 13,000 to 4,000 copies/ml, and the patient's weight had increased from 81.5 to 90.4 kg. The patient appeared clinically well and had no active medical complaints.

Patient 5 began the protocol complaining of secondary infections (including herpes), ataxia, and numbness of the left arm and left side of the face. Two DMF patches were administered weekly, for an average exposure period of 8 hours. The average weekly dose of DMF was 8.25 g and the resulting peak plasma DMF level averaged 110 mg/l. After 19 weeks, the patient's CD4+ T cell count had increased from 260 to 450 cells/μl, the PCR-measured viral load had decreased from 120,000 to 24,000 copies/ml, and the patient's weight had increased from 75.4 to 84.6 kg. The secondary infections had resolved and the patient appeared clinically well.

Patient 6 began the protocol complaining of poor appetite, forgetfulness, abdominal pain, and severe fatigue that prompted him to consider selling his interest in his business. Two DMF patches were administered once weekly, for an average exposure period of 6 hours. The average weekly dose of DMF was 3.75 g and the resulting peak plasma DMF level averaged 67 mg/l. After 5 weeks, the patient's CD4+ T cell count had increased from 354 to 396 cells/μl, the PCR-measured viral load had decreased from 156,000 to 13,000 copies/ml, and the patient's weight had increased from 56.0 to 58.0 kg. The patient was clinically well, had acquired his business partner's share, and was running the business himself.

Patient 7 began the protocol severely ill. The patient's initial CD4+ T cell count was 29 cell/μl, and the initial PCR-measured viral load was 1,156,000 copies/ml. Treatment was with 1 patch, for an average exposure period of 4 hours. The average weekly dose of DMF was 4.60 g and the resulting peak plasma DMF level averaged 100 mg/l. After the first treatment, the patient's CD4+ T cell count decreased to 14 cells/μl. Treatment was given daily for five days and then continued at weekly intervals. After 9 treatments, the patient's CD4+ T cell count had increased to 35 cells/μl, the PCR-measured viral load had decreased to 9,000 copies/ml, and the patient's weight had increased from 46.5 kg (at commencement of DMF therapy) to 49.0 kg. The patient felt well and had returned to full-time employment.

Patient 8 began the protocol with severe herpetic lesions in the lower back and genitalia. Two DMF patches were given once weekly, for an average exposure period of 8 hours. The average weekly dose of DMF was 6.24 g and the resulting peak plasma DMF level averaged 130 mg/l. After 8 weeks, the patient's CD4+ T cell count had increased from 200 to 240 cells/μl, the PCR-measured viral load had decreased from 1,200,000 to 250,000 copies/ml. The patient's weight had increased from 48.1 to 52.2 kg, and the Herpes lesions had entirely resolved.

Two patients were excluded from the trial, one due to alcohol abuse and one due to viral hepatitis B.

Most patients experienced mild local skin irritation at the area of application after removal of the patches; the skin at the application site had a maculopapular appearance, probably due to intense hydration under the patch. In one case, there was slight blistering that resolved within 24 hours and that did not cause the patient significant discomfort. Most patients experienced mild transient nausea, usually on day three after treatment, which gradually decreased during the treatment protocol; one patient reported moderate transient nausea. Four patients showed transient elevation of liver enzymes, which never exceeded three times the upper limit of normal and which in most cases returned to pre-treatment levels prior to the next dose of DMF. Most instances of elevated liver enzymes were associated with at least one factor unrelated to the treatment protocol (alcohol consumption, hepatitis, and previous anti-HIV therapy with other agents).

Figure 4:
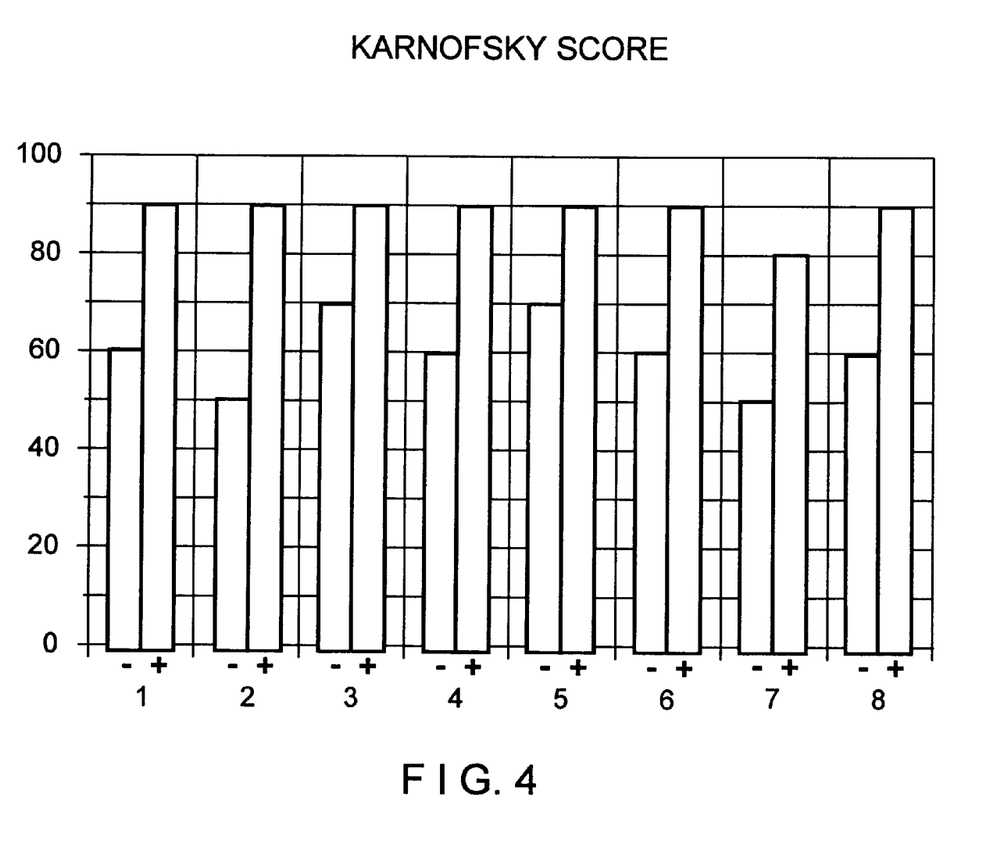
FIG. 4 illustrates the general condition of 8 HIV infected patients, as assessed according to the Karnofsky performance scale before (−) and after (+) treatment with transdermal DMF. See text, Section 8, for details.

Virtually all patients showed clinical improvement after 2–3 weeks of treatment. As shown by FIG. 4, every patient showed improved general condition after treatment with DMF when assessed according to the Karnofsky performance scale, in which a patient's general status is assigned a numerical value as follows: 100=normal, no complaints; 90=able to carry on normal activities, minor signs or symptoms of disease; 80=normal activity with effort; 70=cares for self, unable to carry on normal activity or to do active work; 60=requires occasional assistance, but is able to care for most needs; 50=requires considerable assistance and frequent medical care; 40=disabled, requires special care; 30=severely disabled, hospitalization indicated although death not imminent; 20=very sick, hospitalization and active supportive treatment necessary; 10=moribund, fatal process progressing rapidly; 0=dead. (See Karnofsky et al., 1984, Cancer 1:634–656). Improvement in neurological symptoms and Herpes viral infections was remarkable. Additional anti-microbial therapy for secondary infections was rarely needed. Within the first 14 days of DMF treatment, there was marked improvement in general fatigue and in appetite. All the patients gained weight. Clinical improvement correlated well with disease status as assessed by viral load and CD4+ T cell count. For five out of eight patients, the relative PCR-measured viral load could be fitted to Gompertz curves; this analysis revealed an 88.8% decline in PCR-measured viral load after 42 days of DMF treatment. For seven out of eight patients, the relative CD4+ T cell counts could be fitted to Gompertz curves; this analysis showed a 73.4% increase in CD4+ T cell counts after 42 days of DMF treatment.

The present invention is not to be limited in scope by the exemplified embodiments, which are intended as illustrations of single aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A drug delivery device for transdermal administration of a therapeutic-agent, comprising:

a reservoir containing or having absorbed thereon a therapeutic composition comprising between about 0.25 g and 15.0 g of a therapeutic agent which is N,N'-dimethylformamide (DMF), N-hydroxymethyl-N-methylformamide (HMMF), N-hydroxymethylformamide(HMF), dihydroxymethylformamide (DHMF), N-acetyl, S-(N-methylcarbamoyl) cysteine (AMCC), N-methylformamide (NMF), dimethylsulfoxide (DMSO), formamide, acetamide, methylacetamide, dimethylacetamide, diethylacetamide, isopropylacetamide, diisopropylacetamide, N-acetylpiperidine, N-(β-hydroxyethyl)acetamide, N,N'-di(β-hydroxyethyl)acetamide, N-acetylmorpholine, acrylamide, propionamide, N-fluoromethyl-N-methyl-formamide, pyridine-N-oxide, or an amide of the general formula $R_3$—CO—$NR_1R_2$, in which $R_1$ and $R_2$ are independently selected from the group consisting of H, methyl, halomethyl, saturated and unsaturated $C_2$–$C_3$ alkyl groups, and hydroxylated alkyl groups; or $R_1$ and $R_2$ are together selected from the group consisting of $(CH_2)_4$, $(CH_2)_5$, and $(CH_2)_2O(CH_2)_2$; and $R_3$ is selected from the group consisting of H, methyl, and saturated and unsaturated $C_2$–$C_3$ alkyl groups; and means for maintaining the reservoir in transferring relationship with the skin of an animal to be treated.

2. The drug delivery device according to claim 1, in which the therapeutic composition comprises DMF.

3. The drug delivery device according to claim 2, in which the therapeutic composition comprises DMF in an amount that is effective for treating a viral or microbial infection or a wasting syndrome in a human adult or a human child.

4. A drug delivery device for transdermal administration of a therapeutic agent, comprising:

a backing;

a permeable membrane suitable for placement against the skin of an animal to be treated; and an adsorbent situated between the backing and the permeable membrane, the adsorbent having adsorbed thereon a therapeutic composition comprising between about 0.25 g and 15.0 g of a therapeutic agent which is N,N'-dimethylformamide (DMF), N-hydroxymethyl N-methylformamide (HMMF), N-hydroxymethylformamide (HMF), dihydroxymethylformamide (DHMF), N-acetyl, S-(N-methylcarbamoyl)cysteine (AMCC), N-methylformamide (NMF), dimethylsulfoxide (DMSO), formamide, acetamide, methylacetamide, dimethylacetamide, diethylacetamide, isopropylacetamide, diisopropylacetamide, N-acetylpiperidine, N-(β-hydroxyethyl)acetamide, N,N'-di(β-hydroxyethyl)acetamide, N-acetylmorpholine, acrylamide, propionamide, N-fluoromethyl-N-methyl-formamide, pyridine-N-oxide, or an amide of the general formula $R_3$—CO—$NR_1R_2$, in which $R_1$ and $R_2$ are independently selected from the group consisting of H, methyl, halomethyl, saturated and unsaturated $C_2$–$C_3$ alkyl groups, and hydroxylated alkyl groups; or $R_2$ and $R_2$ are together selected from the group consisting of $(CH_2)_4$, $(CH_2)_5$, and $(CH_2)_2O(CH_2)_2$; and $R_3$ is selected from the group consisting of H, methyl, and saturated and unsaturated $C_2$–$C_3$ alkyl groups;

the drug delivery device adapted to be placed in contact with the skin of an animal to be treated.

5. The drug delivery device according to claim 4, in which the therapeutic composition comprises DMF.

6. The drug delivery device according to claim 5, in which the therapeutic composition comprises DMF in an amount that is effective for treating a viral or microbial infection or a wasting syndrome in a human adult or a human child.

7. The drug delivery device according to claim 4, in which the adsorbent is colloidal silicon dioxide and the permeable membrane is a TEFLON™ (polytetrafluoroethylene) membrane having pores of diameter from about 0.1 µm to about 0.5 µm.

8. The drug delivery device according to claim 7, in which the therapeutic composition comprises DMF.

9. A method of treating a wasting syndrome or a viral or microbial infection comprising administering to an animal in need of treatment a therapeutic composition comprising between about 0.25 g and 15.0 g of a therapeutic agent which is N,N'-dimethylformamide (DMF), N-hydroxymethyl-N-methylformamide (HMMF), N-hydroxymethylformamide (HMF), dihydroxymethylformamide (DHMF), N-acetyl, S-(N-methylcarbamoyl) cysteine (AMCC), N-methylformamide (NMF), dimethylsulfoxide (DMSO), formamide, acetamide, methylacetamide, dimethylacetamide, diethylacetamide, isopropylacetamide, diisopropylacetamide, N-acetylpiperidine, N-(β-hydroxyethyl)acetamide, N,N'-di(β-hydroxyethyl)acetamide, N-acetylmorpholine, acrylamide, propionamide, N-fluoromethyl-N-methylformamide, pyridine-N-oxide, or an amide of the general formula $R_3$—CO—$NR_1R_2$, in which $R_1$ and $R_2$ are independently selected from the group consisting of H, methyl, halomethyl, saturated and unsaturated $C_2$–$C_3$ alkyl groups, and hydroxylated alkyl groups; or $R_1$ and $R_2$ are together selected from the group consisting of $(CH_2)_4$, $(CH_2)_5$, and $(CH_2)_3O(CH_2)_2$; and $R_3$ is selected from the group consisting of H, methyl, and saturated and unsaturated $C_2$–$C_3$ alkyl groups.

10. The method according to claim 9, in which the therapeutic composition is administered for treatment of a wasting syndrome.

11. The method according to claim 9, in which the therapeutic composition is administered for treatment of a retroviral infection.

12. The method according to claim 9, in which the therapeutic composition comprises an amide of the general formula $R_3$—CO—$NR_1R_2$, in which $R_1$ and $R_2$ are independently selected from the group consisting of H, methyl, halomethyl, saturated and unsaturated $C_2$–$C_3$ alkyl groups, and hydroxylated alkyl groups; or $R_1$ and $R_2$ are together selected from the group consisting of $(CH_2)_4$, $(CH_2)_5$, and $(CH_2)_2O(CH_2)_2$; and $R_3$ is selected from the group consisting of H, methyl, and saturated and unsaturated $C_2$–$C_3$ alkyl groups.

13. The method according to claim 12, in which the therapeutic composition comprises an amide of the general formula $R_3$—CO—$NR_1R_2$, in which $R_1$ and $R_2$ are independently selected from the group consisting of H, methyl, halomethyl, saturated and unsaturated $C_2$–$C_3$ alkyl groups, and hydroxylated alkyl groups; and $R_3$ is selected from the group consisting of H, methyl, and saturated and unsaturated $C_2$–$C_3$ alkyl groups.

14. The method according to claim 9, in which the therapeutic composition comprises DMF, HMMF, HMF, DHMF, AMCC, NMF, DMSO, formamide, acetamide, methylacetamide, dimethylacetamide, diethylacetamide, isopropylacetamide, diisopropylacetamide, N-acetylpiperidine, N-(β-hydroxyethyl)acetamide, N,N'-di(β-hydroxyethyl)acetamide, N-acetylmorpholine, acrylamide, propionamide, N-fluoromethyl-N-methyl-formamide, or pyridine-N-oxide.

15. The method according to claim 14, in which the therapeutic composition comprises DMF, HMMF, HMF, DHMF, AMCC, or NMF.

16. The method according to claim 15, in which the therapeutic composition is administered for treatment of a wasting syndrome.

17. The method according to claim 15, in which the therapeutic composition is administered for treatment of a retroviral infection.

18. The method according to claim 17, in which the retroviral infection is an HIV infection.

19. The method according to claim 18, further comprising administering at least one other agent effective for treating HIV infection.

20. The method according to claim 18, further comprising administering at least one nucleoside analog reverse transcriptase inhibitor, at least one non-nucleoside reverse transcriptase inhibitor, or at least one protease inhibitor.

21. The method according to claim 15, in which the therapeutic composition comprises DMF.

22. The method according to claim 21, in which the therapeutic composition is administered for treatment of a wasting syndrome.

23. The method according to claim 22, in which the therapeutic composition is administered transdermally.

24. The method according to claim 21, in which the therapeutic composition is administered for treatment of a retroviral infection.

25. The method according to claim 24, in which the retroviral infection is an HIV infection.

26. The method according to claim 25, in which the therapeutic composition is administered transdermally.

27. The method according to claim 25, further comprising administering at least one other agent effective for treating HIV infection.

28. The method according to claim 25, further comprising administering at least one nucleoside analog reverse transcriptase inhibitor, at least one non-nucleoside reverse transcriptase inhibitor, or at least one protease inhibitor.

29. The method according to claim 14, in which the therapeutic composition comprises DMSO.

30. The method according to claim 29, in which the therapeutic composition is administered for treatment of a wasting syndrome.

31. The method according to claim 30, in which the therapeutic composition is administered by a transdermal route.

32. The method according to claim 29, in which the therapeutic composition is administered for treatment of a retroviral infection.

33. The method according to claim 32, in which the retroviral infection is an HIV infection.

34. The method according to claim 33, in which the therapeutic composition is administered transdermally.

* * * * *